(12) United States Patent
Nieman et al.

(10) Patent No.: US 8,722,653 B2
(45) Date of Patent: *May 13, 2014

(54) METHOD FOR TREATING UTERINE FIBROIDS

(71) Applicants: Laboratoire HRA-PHARMA, Paris (FR); The United States of America, as represented by the Secretary, Department of Health and Human Services, Bethesda, MD (US)

(72) Inventors: Lynnette Nieman, Bethesda, MD (US); Andre Ulmann, Paris (FR); Diana Blithe, Silver Spring, MD (US); Erin Gainer, Paris (FR)

(73) Assignees: Laboratoire HRA-Pharma, Paris (FR); The United States of America, as Represented by the Secretary, Department of Health and Human Services, Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/622,892

(22) Filed: Sep. 19, 2012

(65) Prior Publication Data

US 2013/0023506 A1   Jan. 24, 2013

Related U.S. Application Data

(63) Continuation of application No. 12/021,610, filed on Jan. 29, 2008, now Pat. No. 8,299,050.

(51) Int. Cl.
*A61K 31/56* (2006.01)

(52) U.S. Cl.
USPC ......................................................... 514/178

(58) Field of Classification Search
USPC ......................................................... 514/178
See application file for complete search history.

*Primary Examiner* — Marcos Sznaidman
(74) *Attorney, Agent, or Firm* — Ascenda Law Group PC

(57) ABSTRACT

The invention relates to a method for treating uterine fibroids, which method comprises administering to a patient in need thereof, an effective amount of 17α-acetoxy-11β-[4-N,N-dimethylamino-phenyl)-19-norpregna-4,9-diene-3,20-dione (ulipristal) or any metabolite thereof. More particularly, the method is useful for reducing or stopping bleeding in a patient afflicted with uterine fibroids, and/or for reducing the size of uterine fibroids.

11 Claims, 2 Drawing Sheets

METHOD FOR TREATING UTERINE FIBROIDS

This application is a continuation of U.S. application Ser. No. 12/021,610, filed Jan. 29, 2008.

This invention relates to a method for treating uterine fibroids, also called leiomyomata, or tumors deriving therefrom.

Leiomyomata are common pelvic fibroid tumors occurring in up to 20% of women over 30 years of age. Leiomyomata represent one of the most frequent indications of surgical procedures in woman of reproductive age. Studies show that up to 77% of women have microscopic or macroscopic uterine fibroids at the time of menopause (Cramer et al, 1990). Leiomyomata may be 1 mm to 20 cm in diameter.

Leiomyomata are monoclonal sex-hormone responsive tumors of myometrial cells with abundant extra cellular collagen matrix. The histological appearance is similar to that of normal myometrium surrounded by a pseudocapsule of compressed myometrium, although areas of fibrosis and calcification (thought to represent degeneration) may be present. Leiomyomata are almost always benign in pre-menopausal women but may be indistinguishable from leiomyosarcomas, a tumor most common in post-menopausal women.

While these tumors may be asymptomatic, they frequently have clinical manifestations, such as excessive uterine bleeding, chronic pelvic pain or pressure, or dysmenorrhea, especially when large. Miscarriage and infertility are associated with fibroids as well (Somigliana et al, 2007). However, it is the location, rather than the size of the fibroid that appears related to these last two clinical problems. The treatment of leiomyomata depends on the symptoms, location, and size of the tumor, and the age of the woman. Expectant treatment is recommended for asymptomatic women and medical treatment of menorrhagia for those with excessive bleeding. Because high levels of estradiol cause tumour growth, other approaches include temporizing until menopause, when gonadal steroid levels fall. In other studies, induction of a <<medical menopause>> with low estradiol and progesterone levels by GnRH agonists led to rapid shrinkage of the tumors. However, medical therapy with GnRH agonists causes hot flushes and osteoporosis (the latter when given for more than six months), so they are recommended for use only up to six months. The selective progesterone receptor modulator mifepristone also reduced fibroid size in a dose-dependent manner (Murphy 1995, Zeng 1998).

Because there are no safe and effective long-term medical therapies for leiomyomata, surgical extirpation by hysterectomy or myomectomy remains the major therapeutic option for symptomatic women and accounted for 300,000 hysterectomies and 20,000 myomectomies in 1997 in the United States (Farquhar 2002). In the United States, the annual inpatient cost for these procedures was more than two billion dollars in 1997 (AHRQ report 2001). Thus, the impact of this condition on the public health and health care cost is significant.

The American College of Obstetricians and Gynecologists (ACOG) has defined conditions under which hysterectomy is an appropriate therapy of leiomyoma for women who do not wish to maintain fertility (ACOG Practice Bulletin 1994). These include excessive bleeding, pelvic discomfort or increased urinary frequency or uterine enlargement greater than 12 weeks gestation size that is a concern to the patient. Laparoscopic or hysteroscopic myomectomies may be an alternative to laparotomy or hysterectomy depending on the skill of the laproscopist and whether the fibroids are submucosal and can be accessed by the hysteroscope (ACOG Practice Bulletin 2000). Endometrial ablation to destroy the endometrium targets the source of endometrial bleeding and may be effective when that is the primary symptom. A number of small studies with limited follow-up suggest that uterine artery embolization can decrease bloodflow to the uterus, and reduce leiomyoma and uterine size. However, the procedure may be painful and cause infection and bleeding that leads to surgery. Because of damage to the uterine and ovarian blood supply, it is not recommended for pre-menopausal women interested in preserving fertility. Pregnancy outcomes following this procedure are not well studied.

Clinicians would welcome new medical treatments to reduce fibroid symptoms, e.g. either before menopause or before surgery.

SUMMARY OF THE INVENTION

The invention provides a method for treating uterine fibroids or tumors deriving therefrom, which method comprises administering to a patient in need thereof, an effective amount of ulipristal or of a metabolite thereof.

In a preferred embodiment, the patient is administered with a tablet comprising ulipristal or a metabolite thereof.

Surprisingly enough, the inventors have shown that a low dosage, e.g. a daily dosage of 5 to 15 mg, preferably 10 mg, ulipristal was the most effective.

It is thus proposed to administer ulipristal or a metabolite thereof at a daily dosage of 5 to 15 mg, preferably 10 mg.

The patient may be administered with an oral dosage of ulipristal or of a metabolite thereof during a period of about 2 to about 4 months, which period can be repeated once a year.

Ulipristal or a metabolite thereof is particularly efficient to reduce or stop bleeding in a patient afflicted with uterine fibroids, or to reduce the size of uterine fibroids.

Ulipristal or a metabolite thereof may be useful as a contraceptive while treating the uterine fibroids or tumors derived thereof.

In a particular embodiment, the patient is affected with metastatic leiomyoma, also called metastatic or metastasizing leiomyomatosis.

A subject of the invention is a method for treating metastasizing leiomyomatosis, which method comprising administering to a patient in need thereof, an effective amount of 17α-acetoxy-11β-[4-N,N-dimethylamino-phenyl)-19-norpregna-4,9-diene-3,20-dione (ulipristal) or of a metabolite thereof.

DETAILED DESCRIPTION OF THE INVENTION

Figure 1:
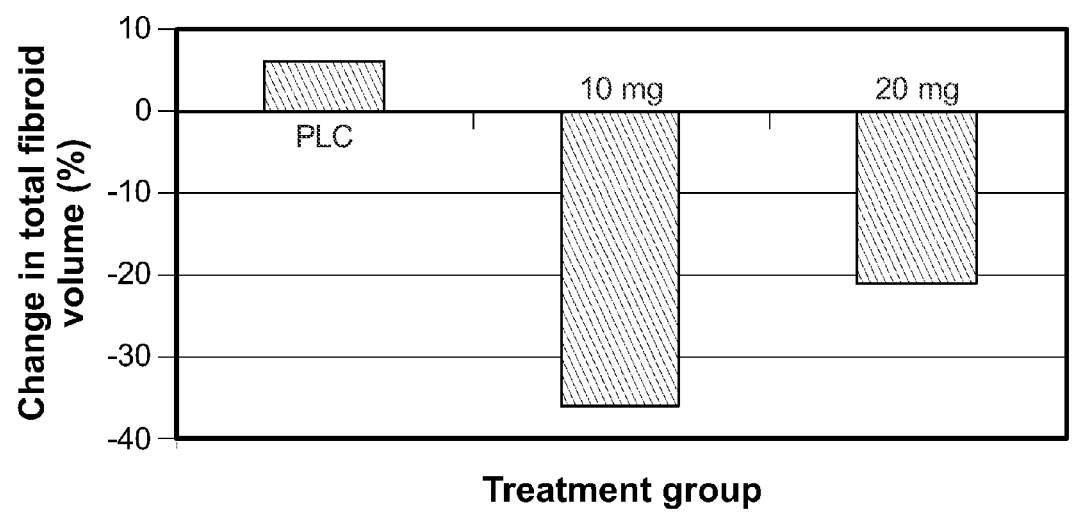
FIG. 1 is a graph that shows the treatment-related change in fibroid volume after 3 months administration with ulipristal (CDB-2914). PLC=placebo; T1=10 mg CDB-2914; T2=20 mg CDB-2914; p=0.01 for T1 or T2 vs. PLC.

Ulipristal, formerly known as CDB-2914, is 17α-acetoxy-11β-[4-N,N-dimethylamino-phenyl)-19-norpregna-4,9-diene-3,20-dione, represented by formula I:

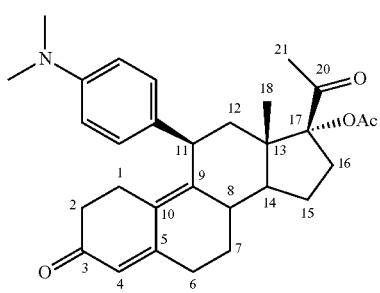

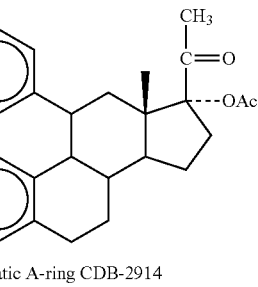

aromatic A-ring CDB-2914

It is a well-known steroid, more specifically a 19-nor-progesterone, which possesses antiprogestational and anti-glucocorticoidal activity. This compound, and methods for its preparation, are described in U.S. Pat. Nos. 4,954,490, 5,073,548, and 5,929,262, and international patent applications WO2004/065405 and WO2004/078709. Properties of this compound are further described in Blithe et al, 2003.

Metabolites of CDB-2914, include those described in Attardi et al, 2004, e.g. monodemethylated CDB-2914 (CDB-3877); didemethylated CDB-2914 (CDB-3963); 17alpha-hydroxy CDB-2914 (CDB-3236); aromatic A-ring derivative of CDB-2914 (CDB-4183).

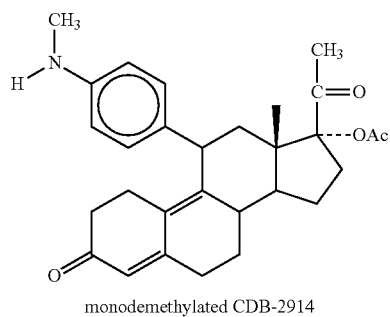

monodemethylated CDB-2914

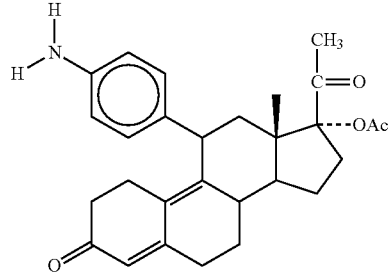

didemethylated CDB-2914

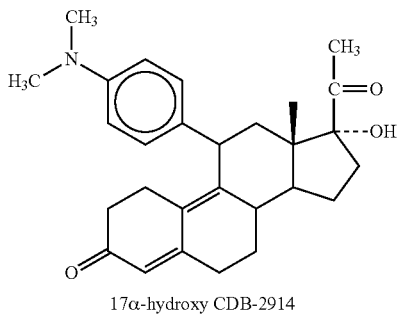

17α-hydroxy CDB-2914

It is now proposed to use ulipristal or a metabolite thereof for treating uterine fibroids, more particularly for reducing or stopping bleeding in a patient afflicted with uterine fibroids, reducing the size of uterine fibroids and/or reducing uterine volume More particularly the inventors have shown in a randomized, placebo-controlled, double blinded, parallel trial, that ulipristal significantly reduces fibroid volume after 3 months, and stops bleeding.

Ulipristal or a metabolite thereof alleviates symptoms of uterine fibroids, including bleeding, pelvic pain, pressure.

Ulipristal or a metabolite thereof is useful for preventing or treating anemia in patients afflicted with uterine fibroids.

It is also useful for preventing or treating leiomyosarcomas and for preventing dissemination of uterine fibroids to other organs.

The inventors further have shown that ulipristal or a metabolite thereof is efficient against pelvic and lung lesions in metastasizing leiomyomatosis after three months.

More generally, the invention relates to a method for treating tumors that derive from leiomyomata, including benign or cancerous tumors, e.g. leiomyosarcomas, leiomyomatosis or metastasizing leiomyomatosis. Metastasizing leiomyomatosis originates from an antecedent leiomyoma of the uterus in virtually all cases. It appears that tumor metastasizes to lungs or other extrauterine tissues via hematogenous spread. However, the origin of the tumor remains controversial.

Drug Delivery:

Ulipristal or a metabolite thereof may be administered by any convenient route, including oral, buccal, parenteral, transdermal, vaginal, uterine, rectal, etc.

For a brief review of present methods for drug delivery, see, Langer, Science 249:1527-1533 (1990), which is incorporated herein by reference. Methods for preparing administrable compounds are known or are apparent to those skilled in the art and are described in more detail in, for example, Remington's Pharmaceutical Science, 17th ed., Mack Publishing Company, Easton, Pa. (1985), which is incorporated herein by reference, and which is hereinafter referred to as "Remington."

For solid compositions, conventional nontoxic solid carriers may be used which include, for example, pharmaceutical grades of mannitol, lactose, starch, magnesium stearate, sodium saccharine, talcum, cellulose, glucose, sucrose, magnesium, carbonate, and the like. For oral administration, a pharmaceutically acceptable nontoxic composition is formed by incorporating any of the normally employed excipients, such as those carriers previously listed.

Oral solid dosage forms preferentially are compressed tablets or capsules. Compressed tablets may contain any of the excipients described above which are diluents to increase the bulk of the ulipristal so that production of a compressed tablet of practical size is possible. Binders, which are agents which impart cohesive qualities to powdered materials are also necessary. Starch, gelatin, sugars such as lactose or dextrose, and natural and synthetic gums are used. Disintegrants are necessary in the tablets to facilitate break-up of the tablet. Disintegrants include starches, clays, celluloses, algins, gums and crosslinked polymers. Lastly small amounts of materials known as lubricants and glidants are included in the tablets to prevent adhesion to the tablet material to surfaces in the manufacturing process and to improve the flow characteristics of the powder material during manufacture. Colloidal silicon dioxide is most commonly used as a glidant and compounds such as talc or stearic acids are most commonly used as lubricants. Procedures for the production and manufacture of compressed tablets are well known by those skilled in the art (See Remington).

Capsules are solid dosage forms using preferentially either a hard or soft gelatin shell as a container for the mixture of ulipristal or a metabolite thereof and inert ingredients. Procedures for production and manufacture of hard gelatin and soft elastic capsules are well known in the art (See Remington).

Buccal forms or devices are also useful, such as those described in U.S. patent application 20050208129, herein incorporated by reference. U.S. patent application 20050208129 describes a prolonged release bioadhesive mucosal therapeutic system containing at least one active principle, with an active principle dissolution test of more than 70% over 8 hours and to a method for its preparation. Said bioadhesive therapeutic system comprises quantities of natural proteins representing at least 50% by weight of active principle and at least 20% by weight of said tablet, between 10% and 20% of a hydrophilic polymer, and compression excipients, and comprising between 4% and 10% of an alkali metal alkylsulphate to reinforce the local availability of active principle and between 0.1% and 1% of a monohydrate sugar.

For parenteral administration, fluid unit dosage forms are prepared utilizing the compounds and a sterile vehicle, water being preferred. Ulipristal or a metabolite thereof, depending on the vehicle and concentration used, can be either suspended or dissolved in the vehicle. In preparing solutions the compound can be dissolved in water for injection and filtered sterilized before filling into a suitable vial or ampoule and sealing. Advantageously, adjuvants such as a local anesthetic, preservative and buffering agents can be dissolved in the vehicle. To enhance the stability, the composition can be frozen after filling into the vial and the water removed under vacuum. The dry lyophilized powder is then sealed in the vial and an accompanying vial of water for injection is supplied to reconstitute the liquid prior to use. Parenteral suspensions can be prepared in substantially the same manner except that the compounds are suspended in the vehicle instead of being dissolved and sterilization cannot be accomplished by filtration. The compound can be sterilized by exposure to ethylene oxide before suspending in the sterile vehicle. Advantageously, a surfactant or wetting agent is included in the composition to facilitate uniform distribution of ulipristal.

Additionally, a suppository can be employed to deliver ulipristal. The active compound can be incorporated into any of the known suppository bases by methods known in the art. Examples of such bases include cocoa butter, polyethylene glycols (carbowaxes), polyethylene sorbitan monostearate, and mixtures of these with other compatible materials to modify the melting point or dissolution rate. These suppositories can weigh from about 1 to 2.5 gm.

Transdermal delivery systems comprising a penetration enhancer and an occlusive backing are of use to deliver ulipristal or a metabolite thereof. Examples of penetration enhancers include dimethyl sulfoxide, dimethyl acetamide and dimethylformamide.

Systems comprising polymeric devices which slowly release or slowly erode and release within the body to provide continuous supplies of ulipristal are also of use. Suitable delivery systems include subcutaneous devices or implants such as those routinely used to deliver norgestrienone or progestin R2323 and other medicaments.

In calculating the dosage for individuals one has to take into consideration the weight of the individual and the mode of administration. The following guidelines provide levels of ulipristal which are clinically effective.

Presuming an average weight of 120 pounds or 53 kilograms, the daily unit dosage of ulipristal is preferably between 5 to 15 mg per day. Surprisingly enough, the reduction of fibroid volume is more important with an oral dose of 10 mg, compared to 20 mg. An oral dose of 10 mg per day is thus most preferred. A lower dosage is also contemplated, e.g. between 1 mg and 10 mg daily, preferably between 5 and 10 mg daily. The oral route is preferred. Other routes of administration can be suitable in comparison with oral routes using blood levels to provide clinical success.

Preferably the amount of ulipristal or a metabolite thereof is effective to alleviate the symptoms of uterine leiomyomata without clinically significant antiglucocorticoid activity.

In a particular embodiment, the patient may be administered with an oral dosage of ulipristal during a period of about 2 to about 4 months.

In a preferred embodiment, the invention provides a method for treating leiomyomata or tumors deriving therefrom in women comprising the administration of a daily dosage of between 5 and 15 mg ulipristal or a metabolite thereof administered orally, in a micronized form.

Once the leiomyomata tumors have fully responded, a maintenance dosage of around mg can be administered over a long period, e.g., in excess of 12 months.

The method according to the invention then further comprises a period of treatment during which a daily dosage of ulipristal or a metabolite thereof is administered, wherein said dosage is administered at less than one half the initial treatment daily dosage.

In a particular embodiment, the treatment period may be repeated once a year, or every two years.

The Patient:

The patient can be any human female, but may also be a non-human mammalian female. The patient may be administered with ulipristal or a metabolite thereof at any time when needed.

However it may be of particular interest to administer ulipristal or a metabolite thereof before undergoing surgery of the uterus or non- or minimally invasive removal or destruction of the fibroids.

Indeed the treatment with ulipristal or a metabolite thereof stops all bleeding and renders the patient amenorrheic, which improves hemostasis and general condition of the patient before surgery. Furthermore it favors non- or minimally invasive removal or destruction of the fibroids, against invasive surgery like myomectomy, hysterectomy. Surgical interventions and uterine artery embolisation can then be performed by means of a laparoscope or transvaginally preferably. Ultrasound or thermal treatment may also be sufficient to destroy the remaining fibroids. ExAblate® device may be useful in that respect. This device provides a uterine-sparing alternative for women that is a non-invasive treatment. It combines two systems—a magnetic resonance imaging (MRI) machine to visualize patient anatomy, map the volume of fibroid tissue to be treated, and monitor the temperature of the uterine tissue after heating, and a focused ultrasound beam that heats and destroys the fibroid tissue using high frequency, high-energy sound waves.

The following examples are provided by way of illustration only and not by way of limitation. Those of skill will readily recognize a variety of noncritical parameters which could be changed or modified to yield essentially similar results.

EXAMPLES

Example 1

Randomized, Placebo-Controlled, Double Blinded, Parallel Trial of the Selective Progesterone Receptor Modulator, Ulipristal (CDB-2914)

Materials and Methods:

Healthy women aged 33-50 years with symptomatic fibroids and regular menstrual cycles were considered for enrollment.

Inclusion criteria included regular cycles and contraceptive use, and symptomatic fibroids as defined by ACOG practice bulletin 1994:

Excessive uterine bleeding evidenced by either of the following: profuse bleeding with flooding or clots or repetitive periods lasting for more than 8 days; or anemia due to acute or chronic blood loss;

or pelvic discomfort caused by leiomyomata, either acute or severe or chronic lower abdominal or low back pressure or bladder pressure with urinary frequency not due to urinary tract infection.

Exclusion criteria included pregnancy, hemoglobin<10 g/dL, current hormone therapy, rapidly enlarging uterus and FSH>20 IU/mL. MR images were obtained to record fibroid number, location and volume, before starting study drug and within 2 weeks of surgery. Women took ulipristal at an oral dose of 10 or 20 mg, or placebo (PLC: microcrystalline cellulose) for 3 cycles, or 90 days if they became anovulatory. The percent change in total fibroid volume was compared. Wilcoxon rank sum test and t-test were used as needed.

Results:

22 women met inclusion criteria and 18 women (72% Black, 28% White) completed the study. The six who received PL had similar mean age and BMI to ulipristal group. Complete data on overall change in fibroid volume as determined by MR imaging were available from the 18 completers. During the three month study interval, the total fibroid volume increased by 6% among those receiving PLC; those receiving 10 mg and 20 mg demonstrated a 36% and 21% reduction in fibroid volume, respectively (see FIG. 1). When the two CDB-2914 groups were combined in comparison to PLC, there was a significant reduction in total fibroid volume after three months of therapy (PLC: 6%; CDB-2914: −29%; p=0.01).

Figure 2:
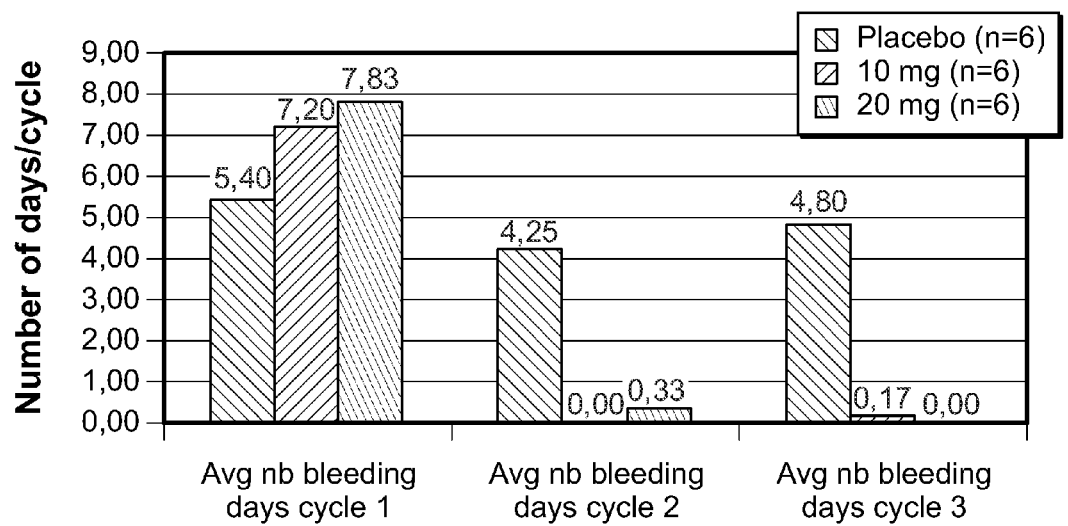
FIG. 2 is a graph that shows the average number of bleeding days by cycle and treatment group, i.e. placebo, 10 mg, or 20 mg ulipristal (CDB-2914) orally.

Additional analyses evaluated treatment-related differences in menstrual function. Women receiving PLC had monthly menses throughout the study interval. On the contrary, there was only a single episode of menstrual bleeding occurring in a subject receiving 10 mg; no woman receiving 20 mg had any bleeding (see FIG. 2). When compared to PLC, CDB-2914 was associated with a significant reduction in menses with evidence of a dose-dependent effect (p<0.001).

One patient had complex endometrial hyperplasia without atypia at surgery.

Conclusions:

Compared to Placebo, ulipristal at 10 or 20 mg daily significantly reduced the size of fibroids by 36% and 21%, respectively, after 90 days, and induced amenorrhea.

Example 2

Gene Expression Profiling Study

Materials and Methods:

Pre-menopausal women with symptomatic fibroids received ulipristal (10 or 20 mg; n-=12) or placebo (PL) (n=6) in a blinded, randomized allocation, for 90 days before hysterectomy. No other hormonal therapy was given. Fibroid tissue and adjacent myometrium were collected at surgery and processed in RNAlater (for RNA isolation). Fibroid tissue also was processed for paraffin embedding (for immunohistochemisty (IHC) and TUNEL assay). Total RNA was used for Affymetrix microarray with the U133 Plus 2.0 human chip. Differential transcription of genes of interest was confirmed by RT-PCR analysis. The TUNEL assay and IHC for Ki67 and phosphorylated histone 3 (phospho H3) were applied to paraffin embedded tissue sections, and the percentage of positive stained cells was noted to assess apoptosis and proliferation. RT-PCR results and proliferation assays were analyzed using two-tailed student t-test; Kruskal-Wallis test was used to assess TUNEL assay results; $P<0.05$ was considered significant.

Results:

Fibroids exposed to ulipristal had increased measures of apoptosis and decreased measures of proliferation, compared to PL. Genomic analysis based on a 2 fold change cut-off and $P<0.02$ identified 314 genes expressed differentially between ulipristal and PL. Eight genes of interest were chosen because of their potential roles in proliferation or apoptosis and the presence of a progesterone response element in the promoter. RT-PCR validated the differential expression of Clusterin (Clu), Fas apoptotic inhibitory molecule 2 (FAIM2), Norrie disease protein (NDP), wingless-type MMTV integration site family, member 5A (Wnt5A), B-cell leukemia/lymphoma 2 (Bcl2), sterile-alpha motif and leucine zipper containing kinase AZK (ZAK), proteolipid protein 1 (PLP1) (see the table below).

Fold change of RT-PCR gene product in ulipristal treated compared to placebo

| Gene name | Fold change | P value |
|---|---|---|
| Clu | −2.1 | 0.019 |
| FAIM | −1.8 | 0.017 |
| NDP | −5.6 | 0.001 |
| Wnt5A | −2.4 | 0.008 |
| Bcl2 | −1.5 | 0.224 |
| ZAK | 1.5 | 0.014 |
| PLP1 | 9.2 | 0.006 |

Conclusion:

Fibroid shrinkage associated with ulipristal treatment is accompanied by increased apoptosis and decreased proliferation and transcriptional changes that potentially underlie these observations.

Example 3

Treatment of Benin Metastatic Leiomyoma

A woman with known benign metastatic leiomyoma status post abdominal surgery that confirmed multiple nodules was treated with ulipristal (daily oral dose of 10-20 mg), in a compassionate protocol. The treatment led to resolution of a right pleural effusion, decrease in a liver nodule and some decrease in two uterine fibroids. More importantly, her pulmonary function tests improved from 50% of predicted to 103% of predicted after 3 months of treatment. She felt better.

REFERENCES

Attardi et al, Journal of Steroid Biochemistry & Molecular Biology, 2004, 88: 277-288
Blithe D L, Nieman L K, Blye R P, Stratton P, Passaro M. Steroids. 2003; 68(10-13):1013-7.
Cramer S F, Patel A. The frequency of uterine leiomyomas. Am J Clin Pathol. 1990; 94(4):435-8.
Farquhar C M, Steiner C A. Hysterectomy rates in the United States 1990-1997. Obstet Gynecol. 2002; 99(2):229-34.
Murphy A A, Morales A J, Kettel L M, Yen S S. Regression of uterine leiomyomata to the antiprogesterone RU486: dose-response effect. Fertil Steril. 1995; 64(1):187-90.
Langer R. New Methods of Drug Delivery. Science 1990; 249:1527-33.
Somigliana E, Vercellini P, Daguati R, Pasin R, De Giorgi O, Crosignani P G. Fibroids and female reproduction: a critical analysis of the evidence. Hum Reprod Update. 2007; 13(5):465-76.
Zeng C, Gu M, Huang H. [A clinical control study on the treatment of uterine leiomyoma with gonadotrophin releasing hormone agonist or mifepristone]. Zhonghua Fu Chan Ke Za Zhi. 1998; 33(8):490-2.

What is claimed:

1. A method for reducing or stopping bleeding in a patient suffering from uterine fibroids, the method comprising administering orally to the patient for at least one menstrual cycle a daily oral dosage ranging from about 5 mg to about 20 mg of 17α acetoxy-11β-[4-N,N-dimethylamino-phenyl)-19-norpregna-4,9-diene-3,20-dione (ulipristal acetate), wherein bleeding is reduced or stopped after the administration of ulipristal acetate for one menstrual cycle.

2. The method of claim 1, wherein the patient is administered orally with a tablet comprising ulipristal acetate.

3. The method of claim 1, wherein the patient is administered orally with a daily dosage of 5 to 15 mg ulipristal acetate.

4. The method of claim 3, wherein the patient is administered orally with a daily dosage of 10 mg ulipristal acetate.

5. The method of claim 3, wherein the patient is administered orally with a capsule comprising ulipristal acetate.

6. The method of claim 1, wherein the patient is administered with ulipristal acetate during a period of about 2 months to about 4 months.

7. The method of claim 6, which is repeated once a year.

8. The method of claim 1, wherein the patient is administered with ulipristal acetate before undergoing surgery of the uterus.

9. The method of claim 1, wherein ulipristal acetate metabolite thereof further acts as a contraceptive.

10. The method of claim 1, wherein the method further decreases the risk of or treats anemia in the patient.

11. The method of claim 1, wherein the method further reduces the size of uterine fibroids in the patient.

* * * * *